United States Patent
Warner et al.

(10) Patent No.: US 9,000,232 B2
(45) Date of Patent: Apr. 7, 2015

(54) EXTRACTIVE DISTILLATION OF CRUDE ALCOHOL PRODUCT

(75) Inventors: R. Jay Warner, Houston, TX (US); Victor J. Johnston, Houston, TX (US); David Lee, Seabrook, TX (US); Adam Orosco, Houston, TX (US)

(73) Assignee: Celanese International Corporation, Irving, TX (US)

( * ) Notice: Subject to any disclaimer, the term of this patent is extended or adjusted under 35 U.S.C. 154(b) by 541 days.

(21) Appl. No.: 13/456,559

(22) Filed: Apr. 26, 2012

(65) Prior Publication Data

US 2012/0277463 A1  Nov. 1, 2012

Related U.S. Application Data

(63) Continuation-in-part of application No. 13/094,588, filed on Apr. 26, 2011, now Pat. No. 8,686,200, and a continuation-in-part of application No. 13/162,034, filed on Jun. 16, 2011, now Pat. No. 8,748,675.

(60) Provisional application No. 61/566,442, filed on Dec. 2, 2011.

(51) Int. Cl.
*C07C 29/149* (2006.01)
*C07C 27/04* (2006.01)
*C07C 29/84* (2006.01)

(52) U.S. Cl.
CPC .............. *C07C 29/149* (2013.01); *C07C 27/04* (2013.01); *C07C 29/84* (2013.01)

(58) Field of Classification Search
CPC ............................... C07C 27/04; C07C 29/149
USPC .................... 568/885, 880, 881, 913, 918
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Knox et al. |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,352,940 A | 10/1982 | Adelman et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,443,639 A | 4/1984 | Pesa et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,559,109 A | 12/1985 | Lee et al. |
| 4,569,726 A | 2/1986 | Berg et al. |
| 4,626,321 A | 12/1986 | Grethlein et al. |
| 4,654,123 A | 3/1987 | Berg et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,886,905 A | 12/1989 | Larkins, Jr. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |

(Continued)

FOREIGN PATENT DOCUMENTS

| | | |
|---|---|---|
| CN | 201768393 | 3/2011 |
| CN | 102228831 | 11/2011 |

(Continued)

OTHER PUBLICATIONS

International Preliminary Report on Patentability for PCT/US2012/035196 mailed Nov. 7, 2013.
Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).

(Continued)

*Primary Examiner* — Elvis O Price

(57) ABSTRACT

Recovery of ethanol from a crude ethanol product obtained from the hydrogenation of acetic acid using an extractive distillation column. The column yields a first residue that comprises ethanol, ethyl acetate, acetic acid, and water. The first residue is separated in a second column to yield a second distillate comprising ethanol and ethyl acetate. The second distillate is then separated in a third column to yield a third distillate comprising ethyl acetate and a third residue comprising ethanol.

21 Claims, 7 Drawing Sheets

(56) References Cited

U.S. PATENT DOCUMENTS

| | | |
|---|---|---|
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,198,592 A | 3/1993 | Van Beijnum et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Gaddy et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,834,223 B2 | 11/2010 | Atkins |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey |
| 2009/0221725 A1 | 9/2009 | Chornet et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Weiner et al. |
| 2010/0137630 A1 | 6/2010 | Garton et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010437 A1 | 1/2012 | Jevtic |
| 2012/0010438 A1 | 1/2012 | Lee et al. |
| 2012/0010439 A1 | 1/2012 | Jevtic |
| 2012/0010445 A1 | 1/2012 | Johnston et al. |
| 2012/0273338 A1 | 11/2012 | Lee |
| 2012/0277481 A1 | 11/2012 | Warner |
| 2012/0323049 A1 | 12/2012 | Lee |
| 2012/0323050 A1 | 12/2012 | Lee |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0990638 | 4/2000 |

(56) References Cited

FOREIGN PATENT DOCUMENTS

| | | |
|---|---|---|
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |
| WO | WO 2011/097193 | 8/2011 |
| WO | WO 2011/097219 | 8/2011 |
| WO | WO 2011/097220 | 8/2011 |
| WO | WO 2011/097227 | 8/2011 |
| WO | WO 2011/140485 | 11/2011 |
| WO | WO 2012/006219 | 1/2012 |
| WO | WO 2012/006228 | 1/2012 |
| WO | WO 2012/006499 | 1/2012 |

OTHER PUBLICATIONS

J. Jones, et al., Platinum Metals Review, vol. 44, No. 3, pp. 94-104 (Jul. 2000).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Witzeman and Agreda, "Safety and Performance Assessment of Ethanol/Diesel Blends (e-blend)" NREL/SR-540-34817, at p. 1-1, Sep. 2003.

V. Ragaini et al., "Increasing the value of dilute acetic acid streams through esterification Part 1. Experimental analysis of the reaction zone", Applied Catalysis B: Environmental, vol. 64, 2006, pp. 66-71.

Anonymous: "Studies in Extractive and Azeotropic Distillation Series; Study No. 4—Separation of Alcohols from the Acetate/Alcohol/Water Ternary by Extractive Distillation" May 9, 2008, pp. 1-9.

Kita H., et al., "Synthesis of a Zeolite NAA Membrane for Pervaporation of Water/Organic Liquid Mixtures", Journal of Materials Science Letters, vol. 14, Jan. 1, 1995, pp. 206-208.

Calvar, et al., "Esterification of acetic acid and ethanol: Reaction kinetics and operation in a packed bed reactive distillation column", Chem Engineering and Processing, vol. 46, No. 12, Oct. 9, 2007, pp. 1317-1323.

Marian Simo, et al., "Adsorption/Desorption of Water and Ethanol on 3A Zeolite in Neo-Adiabatic Fixed Bed", Industrial and Engineering Chemistry Research, vol. 48, No. 20, Sep. 25, 2009, pp. 9247-9260.

Benson, Tracy J., et al., "Cellulose Based Adsorbent Materials for the Dehydration of Ethanol Using Thermal Swing Adsorption", Adsorption, Kluwer Academic Publishers, vol. 11, No. 1, Jul. 1, 2005, pp. 697-701.

Yu Huang, et al., "Low-Energy Distillation-Membrane separation Process", Industrial & Engineering Chemistry Research, Am. Chem. Soc., vol. 49, No. 8, Jan. 1, 2010, pp. 3760-3768.

International Search Report and Written Opinion for PCT/US2011/023276 mailed Sep. 2, 2011.

International Search Report and Written Opinion for PCT/US2012/035273 mailed Jul. 30, 2012.

International Search Report and Written Opinion for PCT/US2012/035220 mailed Aug. 2, 2012.

International Search Report and Written Opinion for PCT/US2012/035189 mailed Jul. 30, 2012.

International Search Report and Written Opinion for PCT/US2012/035196 mailed Aug. 6, 2012.

International Search Report and Written Opinion for PCT/US2011/059889 mailed Jul. 6, 2012.

International Search Report and Written Opinion for PCT/US2012/035203 mailed Jul. 11, 2012.

International Search Report and Written Opinion for PCT/US2011/059894 mailed Jun. 13, 2012.

Response to Final Office Action for U.S. Appl. No. 13/094,488 filed Oct. 18, 2013.

Response to Final Office Action for U.S. Appl. No. 13/094,610 filed Oct. 18, 2013.

Response to Final Office Action for U.S. Appl. No. 13/162,005 filed Nov. 26, 2013.

Response to Final Office Action for U.S. Appl. No. 13/094,661 filed Nov. 25, 2013.

Response to Final Office Action for U.S. Appl. No. 13/162,034 filed Nov. 27, 2013.

Jakobsson, et al., "Modelling of a side reactor configuration combining reaction and distillation", Chemical Engineering Science, vol. 57, No. 9, May 1, 2002, pp. 1521-1524.

Xu, et al., "Kinetics of Acetic Acid Esterification Over Ion Exchange Catalysts", Canadian Journal of Chemical Engineering, vol. 74, Aug. 1, 1996, pp. 493-500.

H. Constantin et al., "Influence of C-Sources on the Denitrification Rate of a High-Nitrate Concentrated Industrial Wastewater", Wat. Res. vol. 31, No. 3, 1997, pp. 583-589.

Y. Zhu et al., "Techno-economic Analysis for the Thermochemical Conversion of Lignocellulosic Biomass to Ethanol via Acetic Acid Synthesis", Apr. 1, 2009, pp. 1-71 (80 Pages).

International Search Report and Written Opinion for PCT/US2012/035198 mailed Oct. 30, 2012.

International Search Report and Written Opinion for PCT/US2012/035208 mailed Nov. 9, 2012.

International Search Report and Written Opinion for PCT/US2012/035271 mailed Nov. 12, 2012.

International Search Report and Written Opinion for PCT/US2012/035194 mailed Nov. 15, 2012.

International Search Report and Written Opinion for PCT/US2012/035175 mailed Nov. 15, 2012.

International Search Report and Written Opinion for PCT/US2011/060014 mailed Jun. 29, 2012.

International Search Report and Written Opinion mailed Apr. 19, 2012 in corresponding International Application No. PCT/US2011/060019.

EXTRACTIVE DISTILLATION OF CRUDE ALCOHOL PRODUCT

CROSS REFERENCE TO RELATED APPLICATIONS

This application claims priority to U.S. App. No. 61/566,442, filed on Dec. 2, 2011, the entirety of which is incorporated herein by reference. This application is a continuation-in-part of U.S. application Ser. No. 13/094,588, filed on Apr. 26, 2011 and U.S. application Ser. No. 13/162,034, filed on Jun. 16, 2011, the entireties of which are incorporated herein by reference.

FIELD OF THE INVENTION

The present invention relates generally to processes for producing ethanol from acetic acid in a hydrogenation reactor and, in particular, to an extractive distillation process for recovering ethanol.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP2060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

Others have proposed various extractive agents for separating mixtures of ethanol, ethyl acetate and water. U.S. Pat. No. 4,654,123 describes a process for separating ethanol from water using extractive agents. U.S. Pat. Nos. 4,379,028 and 4,569,726 describe processes for recovering ethyl acetate from an ethyl acetate/ethanol/water mixture using extractive agents. U.S. Pat. No. 6,375,807 describes a method of separating ethanol and ethyl acetate using extractive agents.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising the steps of hydrogenating acetic acid from an acetic acid feed stream in a reactor to form a crude ethanol product, and separating at least a portion of the crude ethanol product in a first column in the presence of one or more extractive agents selected from a group consisting of water, dimethylsulfoxide, glycerine, diethylene glycol, 1-naphthol, hydroquinone, N,N'-dimethylformamide, 1,4-butanediol, ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'dimethyl-1,3-propanediamine, N,N'-dimethylethylenediamine, diethylene triamine, hexamethylene diamine, 1,3-diaminopentane, and alkylated thiopene, dodecane, tridecane, tetradecane, chlorinated paraffins, and mixtures thereof, into a first distillate comprising acetaldehyde and ethyl acetate and a first residue comprising ethanol, ethyl acetate, and the one or more extractive agents. In one embodiment, the first residue may comprises less than 5 wt. % ethyl acetate. The process further comprises separating at least a portion of the first residue in a second column to yield a second distillate comprising ethanol and ethyl acetate and a second residue comprising the one or more extractive agents, separating at least a portion of the second distillate to yield a third distillate comprising ethyl acetate and a third residue comprising ethanol. In one embodiment at least a portion of the second residue is returned to the first column as the one or more extractive agents and the second residue may comprise less than 30 wt. % acetic acid. In one embodiment, first distillate column may operate at a pressure of less than 70 kPa, e.g., less than 50 kPa, or less than 20 kPa.

In a second embodiment, the present invention is directed to a process for producing ethanol comprising the steps of providing a crude ethanol product comprising ethanol, acetic acid, ethyl acetate, acetaldehyde, and water, separating at least a portion of the crude ethanol product in a first column in the presence of one or more extractive agents into a first distillate comprising acetaldehyde and ethyl acetate and a first residue comprising ethanol, ethyl acetate, and the one or more extractive agents, separating the first residue in a second column to yield a second distillate comprising ethanol and ethyl acetate and a second residue comprising the one or more extractive agents, and separating at least a portion of the second distillate to yield a third distillate comprising ethyl acetate and a third residue comprising ethanol.

In a third embodiment, the present invention is directed to a process for producing ethanol comprising the steps of hydrogenating acetic acid from an acetic acid feed stream in a reactor to form a crude ethanol product, separating at least a portion of the crude ethanol product in a first column in the presence of a water extractive agent into a first distillate comprising acetaldehyde and ethyl acetate and a first residue comprising ethanol, water and acetic acid, separating the first residue in a second column to yield a second distillate comprising ethanol and a second residue comprising water and acetic acid, and recovering ethanol from the second distillate.

In one embodiment, the process may comprise separating at least a portion of the second residue to form a water stream and an acetic acid stream. The acetic acid stream may be returned to the reactor and the water stream returned to the first distillation column as an extractive agent. The separation of water and acetic acid may use an adsorption unit, a membrane, a distillation column, and combinations thereof.

In another embodiment, the process further comprises reacting the acetic acid from the second residue with at least one alcohol, preferably methanol, in an esterification unit to produce at least one ester and water, and separating the at least one ester from the water to produce an ester product stream comprising the at least one ester and a aqueous stream comprising water. The aqueous stream may be returned to the first distillation column as an extractive agent.

In a fourth embodiment, the present invention is directed to a process for producing ethanol comprising the steps of hydrogenating acetic acid from an acetic acid feed stream in a reactor to form a crude ethanol product, separating at least a portion of the crude ethanol product in a first column, operating at a pressure of less than 70 kPa, e.g., less than 50 kPa, or less than 20 kPa, in the presence of a water extractive agent into a first distillate comprising acetaldehyde and ethyl acetate and a first residue comprising ethanol, water and acetic acid, separating the first residue in a second column to yield a second distillate comprising ethanol and a second residue comprising water and acetic acid, and recovering ethanol from the second distillate.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Figure 1:
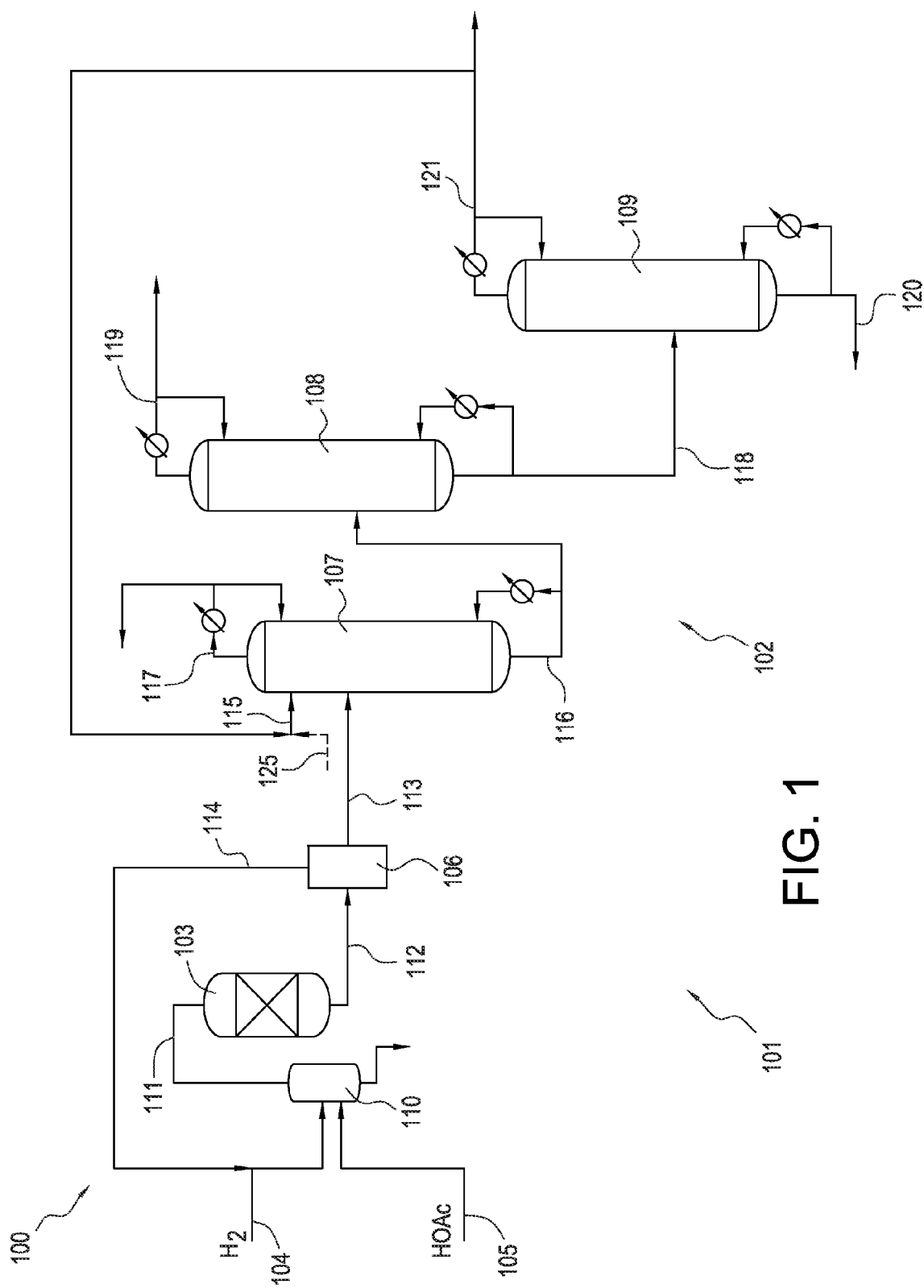
FIG. 1 is a schematic diagram of an ethanol production system with distillation columns to recover the extractive agent from acetic acid in accordance with one embodiment of the present invention.

The present invention relates to processes for recovering ethanol produced by hydrogenating acetic acid in the presence of a catalyst. The hydrogenation reaction produces a crude ethanol product that comprises ethanol, water, ethyl acetate, acetic acid, and other impurities. Ethyl acetate is difficult to separate from a mixture of ethyl acetate and ethanol by distillation because of the closeness in boiling points between ethyl acetate and ethanol. The presence of other components in the crude ethanol product such as ethyl acetate, acetic acid and acetaldehyde, depending on concentration, may further complicate the separation of ethanol and ethyl acetate.

To improve efficiencies in recovering ethanol from the crude ethanol product, the processes of the present invention involve recovering ethanol from the crude ethanol product using one or more extractive agents in an initial (first) separation column. Ethanol, water, and acetic acid are withdrawn as the residue. Ethyl acetate and other light organics are withdrawn as the distillate. The presence of the extractive agents allows the ethanol product to be separated from the ethyl acetate by-product more effectively. Using an extractive agent in accordance with embodiments of the present invention allows for a majority of the ethyl acetate to be recovered from the crude ethanol product. Preferably, at least 90% of the ethyl acetate in the crude ethanol product is recovered through the first distillate, e.g., at least 95% of the ethyl acetate or at least 98% of the ethyl acetate. Recovering a majority of the ethyl acetate provides for low concentrations of ethyl acetate in the residue from the initial column, e.g., less than 1 wt. %, less than 0.3 wt. % or less than 0.01 wt. %. By using one or more extractive agents, an ethanol product may be recovered having a reduced ethyl acetate content. Preferably, at least 50% of the ethanol in the crude ethanol product is recovered in the first residue stream, and more preferably at least 90% of the ethanol.

Advantageously, this separation approach using an extractive agent results in reducing energy requirements to recover ethanol from the crude ethanol product.

The extractive agent for use in the present invention may vary. The extractive agent preferably has a boiling point higher than major components in the distillate. In preferred embodiments, the extractive agent employed has a boiling point greater than 80° C., e.g., greater than 85° C., or greater than 100° C. Extractive agents having boiling points greater than 200° C. are also contemplated. A preferred extractive agent comprises water. The water may be produced in the hydrogenation reactor and recycled as the extractive agent. Preferably, at least one of the extractive agents is a co-product of the ethanol produced by hydrogenation acetic acid. By using a co-product as an extractive agent, the cost of addition and recovery of the extractive agent may be reduced.

In one embodiment, the co-product is water and the water is purified by removing ethanol and/or acetic acid. Purifying the water may reduce the recycling of other components that may lead to side reactions in the columns. The water may be purified by the using of water separation units, such as adsorption units or membranes, or an esterification unit that reacts the acetic acid. The purification of the water also allows recovery of acetic acid that may be returned to the reactor.

In another embodiment the co-product water may be part of a dilute acid stream that does not require as intensive purification. Although not limited to, a dilute acid stream may be preferred when the hydrogenation achieves high conversions of acetic acid, of greater than 80%, greater than 90% or greater than 95%. Thus, the dilute acid stream may reduce the overall energy requirements while stilling maintaining an efficient separation in the initial column. A dilute acid stream may comprise at least 40 wt. % water, e.g., at least 60 wt. % water or at least 80 wt. % water. The dilute acid stream may comprise acetic acid. For example, the extractive agent may comprise less than 30 wt. % acetic acid, e.g., less than 20 wt. %, less than 10 wt. % or less than 5 wt. %. Without being bound by theory the acetic acid in the dilute acid stream may not necessarily act as an extractive agent, it may reduce the amount of ethanol, water, and/or acetic acid that is carried over into the distillate of the initial column.

Other suitable extractive agents may also be used, and may include, for example, dimethylsulfoxide, glycerine, diethylene glycol, 1-naphthol, hydroquinone, N,N'-dimethylformamide, 1,4-butanediol, ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'dimethyl-1,3-propanediamine, N,N'-dimethylethylenediamine, diethylene triamine, hexamethylene diamine, 1,3-diaminopentane, alkylated thiopene, dodecane, tridecane, tetradecane, chlorinated paraffins, and mixtures thereof. These other agents may be used with water. Some suitable extraction agents include those described in U.S. Pat. Nos. 4,379,028; 4,569,726; 5,993,610; and 6,375,807, the entireties of which are incorporated herein by reference.

In one embodiment, the extractive agents may be fed to the initial column for processing the crude ethanol product. In another embodiment, the extractive agents are fed to and combined with the crude ethanol product prior to being introduced into the initial column. Preferably, a substantial portion of the ethanol, water, and acetic acid is removed from the crude ethanol product as the residue from the initial column. The residue stream, for example, may comprise from 30% to 99.5% of the water and from 85% to 100% of the acetic acid from the crude ethanol product. The residue stream may also comprise the extractive agent, water, and thus the water concentration in the residue may exceed the water concentration of the crude ethanol product. The extractive agents may be recovered from the residue, e.g., in one or more additional separation columns, and recycled to the initial column.

Generally, the distillate from the initial column may comprise ethyl acetate and acetaldehyde. The distillate may be recycled in whole or part to the hydrogenation reactor. In some embodiments, the distillate from the initial column may also comprise ethanol and preferably less than 15 wt. % water, less than 7.5 wt. % water, less 4 wt. % water or less than 2 wt. % water. A further extractive column may be used to remove the ethanol from the distillate. In another embodiment, a light ends column may be used to further separate the distillate into an ethyl acetate stream, which is recycled to the hydrogenation reactor, and an ethanol stream.

Although the embodiments of the present invention generally reduce the amount of the ethyl acetate in the residue, ethyl acetate may be present due to further esterification. Any ethyl acetate in the residue is preferably separated to yield a purified ethanol stream. Generally, a separate column may be necessary when the residue comprise at least 50 wppm ethyl acetate or if there is esterification. When the ethyl acetate is less than 50 wppm it may not be necessary to use a separate column to separate ethyl acetate and ethanol. Ethyl acetate separated from the residue may be returned to the initial column and removed as a first distillate. This returned ethyl acetate stream may be fed to the initial column at a point below the extractive agent feed location.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180 and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a syngas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed. Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system so that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489 and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments, the catalyst may be a bulk catalyst.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin, and cobalt.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 99 wt. %, or from 80 to 97.5 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The support may be a modified support and is present in an amount from 0.1 to 50 wt. %, e.g., from 0.2 to 25 wt. %, from 1 to 20 wt. %, or from 3 to 15 wt. %, based on the total weight of the catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary components ranges of the crude ethanol are provided in Table 1, excluding hydrogen. The "other" components identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with higher conversion, and the acetic acid concentration may range from 0.01 wt. % to 20 wt. %, e.g., 0.05 wt. % to 15 wt. %, from 0.1 wt. % to 10 wt. % or from 1 wt. % to 5 wt. %. In embodiments having lower amounts of acetic acid, the conversion of acetic acid in the reactor is preferably greater than 75%, e.g., greater than 85% or greater than 90%. In addition, the selectivity to ethanol may also be preferably high, and is preferably greater than 75%, e.g., greater than 85% or greater than 90%.

In one embodiment, the weight ratio of ethanol to water may be at least 0.18:1 or greater, e.g., at least 0.5:1 or at least 1:1. In terms of ranges the weight ratio of ethanol to water may be from 0.18:1 to 5:1, e.g., from 0.5:1 to 3:1 or from 1:1 to 2:1. Preferably the crude ethanol product has more ethanol than water compared to conventional fermentation processes of ethanol. In one embodiment, the lower amounts of water may require less energy to separate the ethanol and improves the overall efficiency of the process. Thus, in preferred embodiments, the amount of ethanol in the crude ethanol product is from 15 wt. % to 70 wt. %, e.g., from 20 wt. % to 70 wt. % or from 25 wt. % to 70 wt. %. Higher ethanol weight percentages are particularly preferred.

Figure 2:
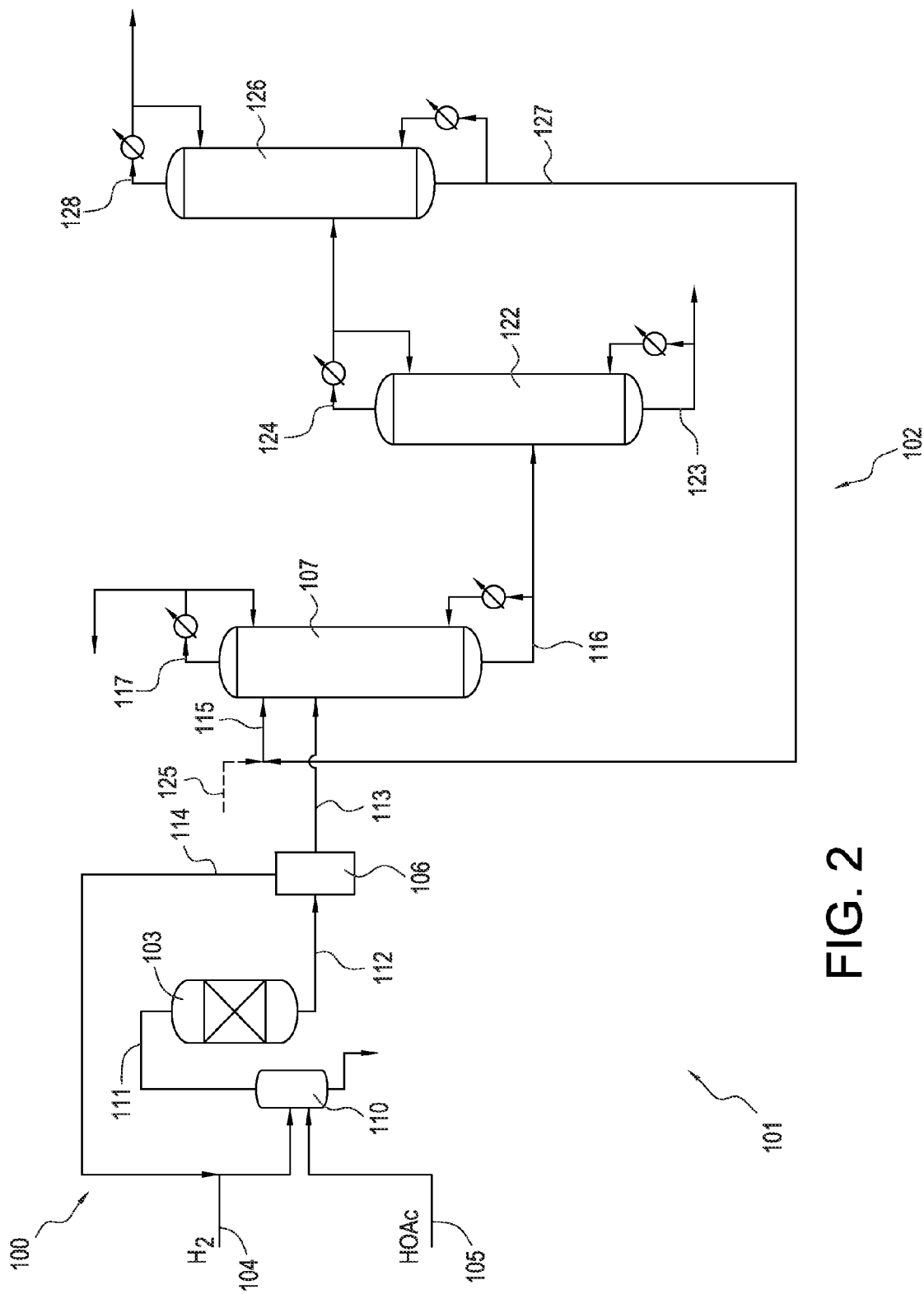
FIG. 2 is a schematic diagram of an ethanol production system with distillation columns to recover the extractive agent from ethanol in accordance with one embodiment of the present invention.
Figure 3:
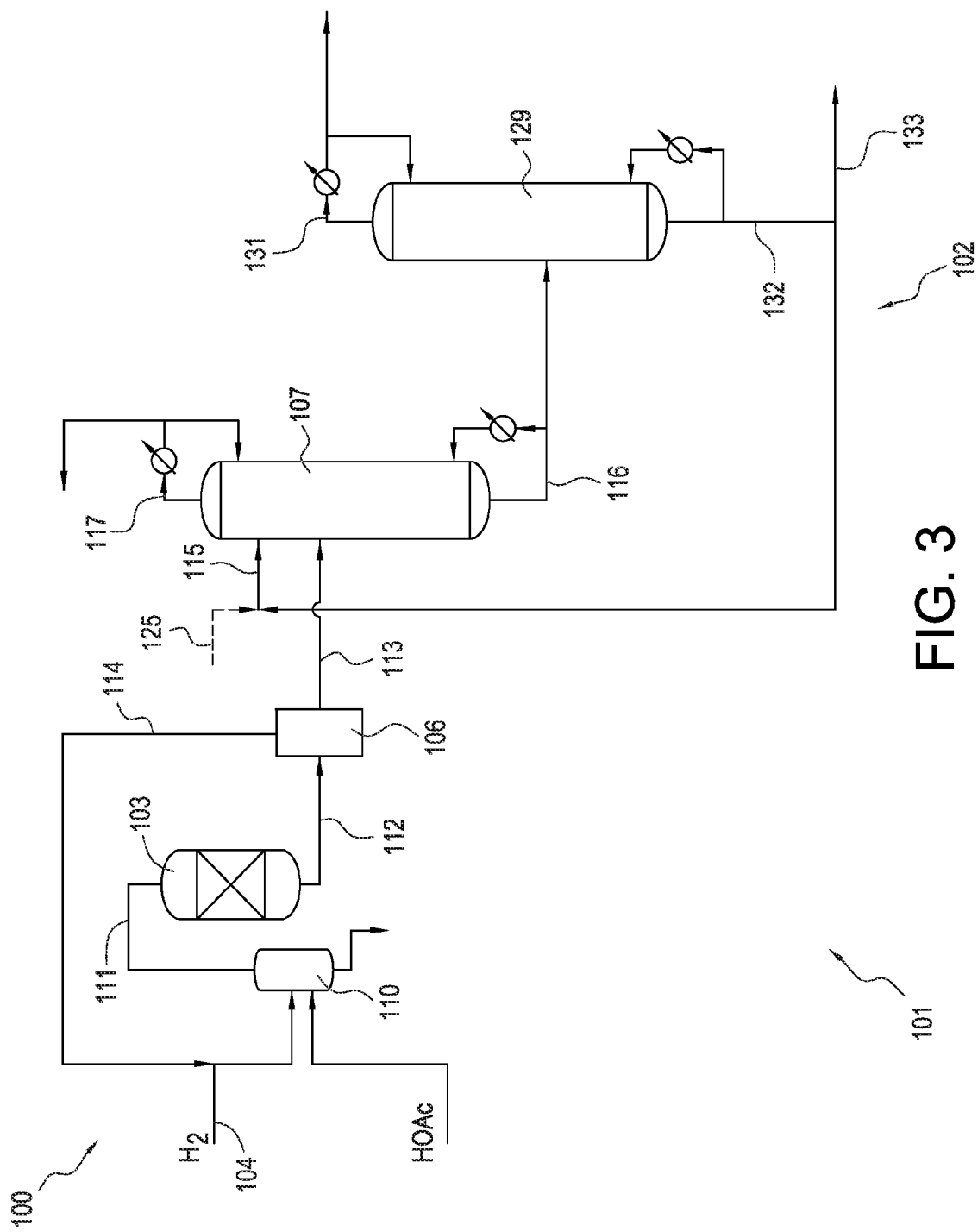
FIG. 3 is a schematic diagram of an ethanol production system with distillation columns to recover a dilute acid stream that is suitable for use as an extractive agent in accordance with one embodiment of the present invention.
Figure 4:
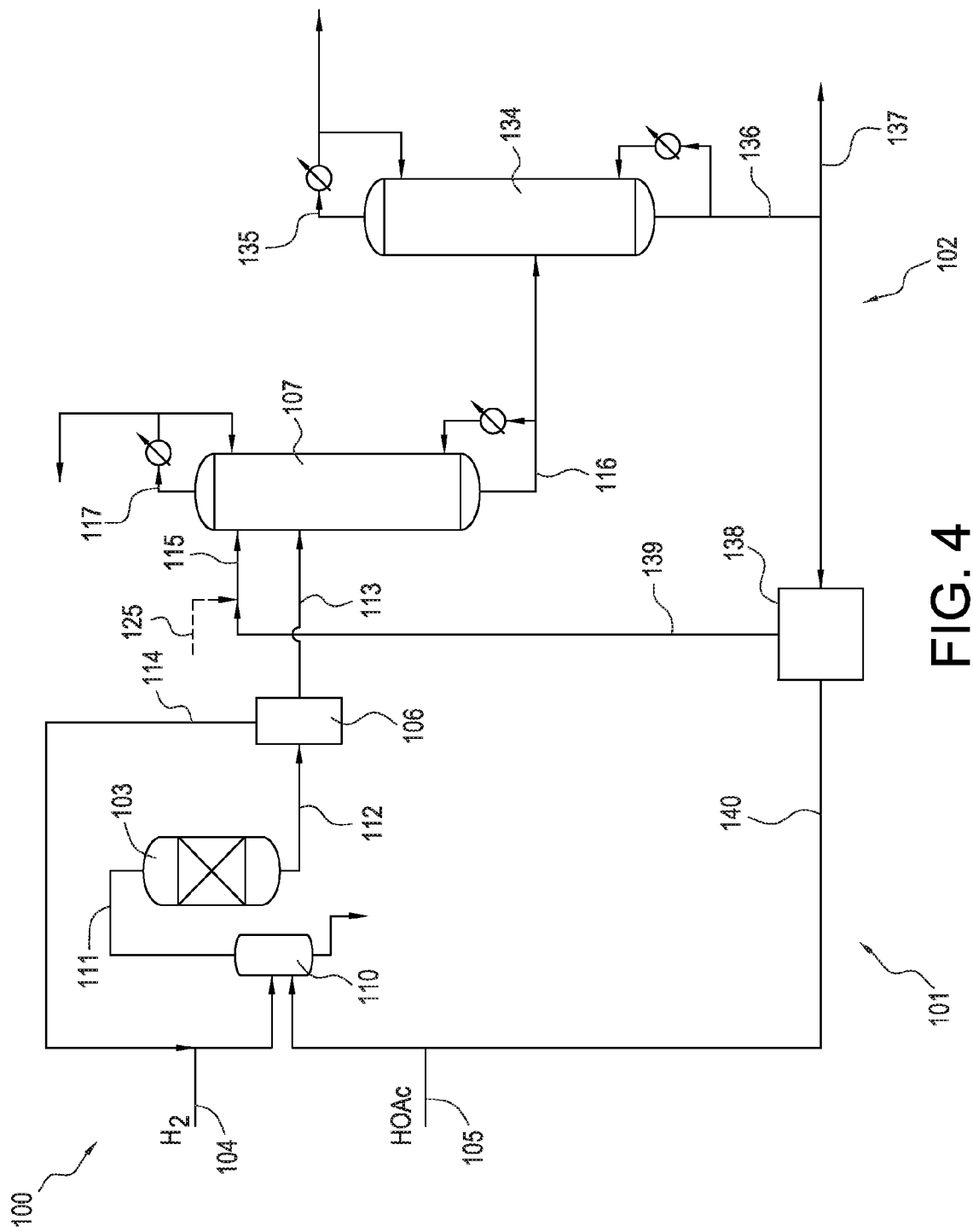
FIG. 4 is a schematic diagram of an ethanol production system with distillation columns to recover the extractive agent using one or more water separation devices to separate acetic acid that is returned to the reactor and water that is returned as an extractive agent, in accordance with one embodiment of the present invention.
Figure 5:
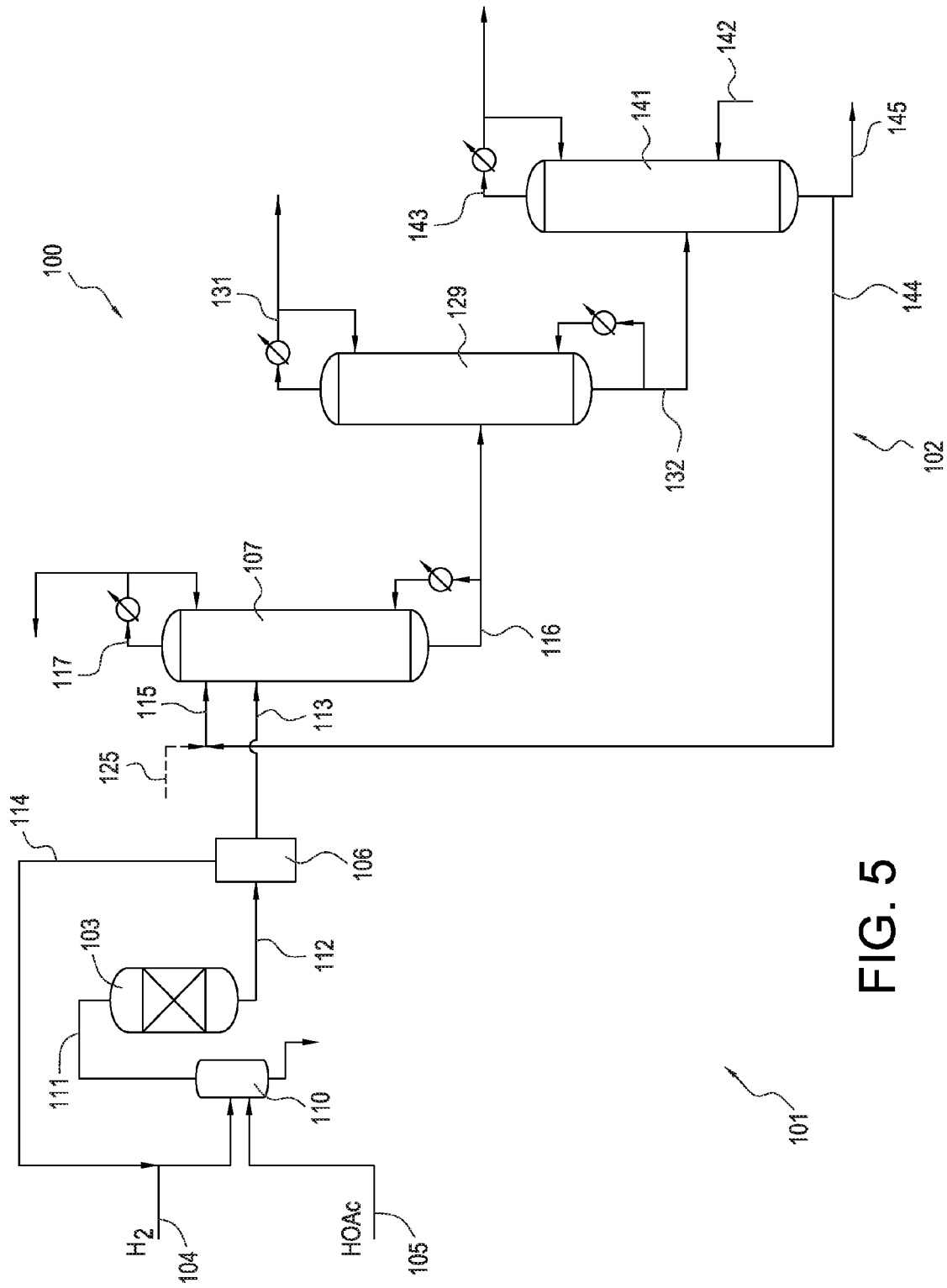
FIG. 5 is a schematic diagram of an ethanol production system with distillation columns to recover the extractive agent and an esterification unit in accordance with one embodiment of the present invention.
Figure 6:
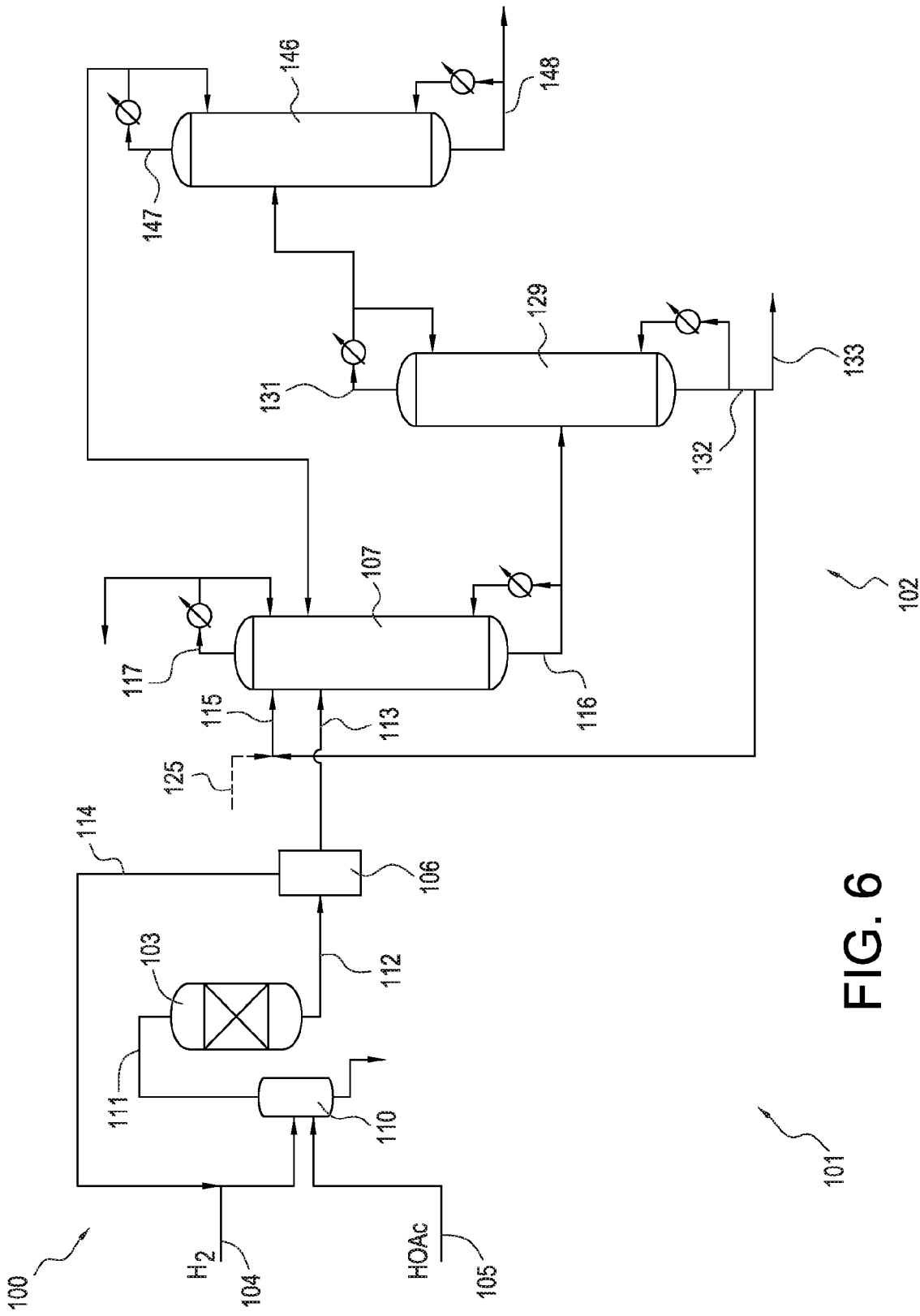
FIG. 6 is a schematic diagram of an ethanol production system with distillation columns to recover a dilute acid stream and a further column for separating ethyl acetate and ethanol, in accordance with one embodiment of the present invention.

Exemplary ethanol recovery systems in accordance with embodiments of the present inventions are shown in FIGS. 1-7. Each hydrogenation system 100 includes a suitable hydrogenation reactor and a process for separating ethanol from the resulting crude ethanol mixture. System 100 comprises reaction zone 101 and separation zone 102. FIGS. 1, 2, 4, 5, and 7 illustrate exemplary systems that recover purified water that is co-product as the extractive agent. FIGS. 3 and 6 illustrate exemplary systems that recover a dilute acid stream as the extractive agent.

As shown in FIGS. 1-7, reaction zone 101 comprises reactor 103, hydrogen feed line 104 and acetic acid feed line 105. Hydrogen and acetic acid are fed to vaporizer 110 via lines 104 and 105, respectively, to create a vapor feed stream in line 111 that is directed to reactor 103. The feed to reactor 103 comprises fresh acetic acid. In one embodiment, lines 104 and 105 may be combined and jointly fed to vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, via a blowdown stream. In addition, although line 111 is shown as being directed to the top of reactor 103, line 111 may be directed to the side, upper portion, or bottom of reactor 103.

Reactor 103 contains the catalyst that is used in the hydrogenation of the carboxylic acid, preferably acetic acid, to ethanol. In one embodiment, one or more guard beds (not shown) may be used upstream of the reactor, optionally upstream of vaporizer 110, to protect the catalyst from poisons or undesirable impurities contained in the feed or return/recycle streams. Such guard beds may be employed in vapor stream 114 or liquid stream 113. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 112.

The crude ethanol product in line 112 may be condensed and fed to a separator 106, which, in turn, provides vapor stream 114 and liquid stream 113. Separator 106, for example, may comprise one or more flashers or knockout pots. Separator 106 may operate at a temperature from 20° C. to 350° C., e.g., from 30° C. to 325° C. or from 60° C. to 250° C. The pressure of separator 106 may be from 100 kPa to 3000 kPa, e.g., from 125 kPa to 2500 kPa or from 150 kPa to 2200 kPa. Optionally, the crude ethanol product in line 112 may pass through one or more membranes to separate hydrogen and/or other non-condensable gases.

Vapor stream 114 exiting separator 106 may comprise hydrogen and hydrocarbons, and may be purged and/or returned to reaction zone 101. As shown, vapor stream 114 is combined with hydrogen feed 104 and co-fed to vaporizer 110. In some embodiments, the returned vapor stream 114 may be compressed before being combined with hydrogen feed 104.

Liquid stream 113 from separator 106 is withdrawn and pumped to first column 107, also referred to as an "extractive column." Liquid stream 113 may be heated from ambient temperature to a temperature of up to 70° C., e.g., up to 50° C., or up to 40° C. The additional energy required to pre-heat liquid stream 113 above 70° C. does not achieve the desired energy efficiency in first column 107 with respect to reboiler duties. In another embodiment, liquid stream 113 is not separately preheated, but is withdrawn from separator 106, and cooled if needed, at a temperature of less than 70° C., e.g., less than 50° C., or less than 40° C., and directly fed to first column 107.

In one embodiment, the contents of liquid stream 113 are substantially similar to the crude ethanol product of line 112 obtained from the reactor, except that the composition has been depleted of hydrogen, carbon dioxide, methane and/or ethane, which are preferably removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

FEED COMPOSITION TO COLUMN 107
(Liquid Stream 113)

|  | Conc. (wt. %) | Conc. (wt. %) | Conc. (wt. %) |
| --- | --- | --- | --- |
| Ethanol | 5 to 72 | 10 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |

The amounts indicated as less than (<) in the tables throughout the present application are preferably not present and if present may be present in amounts greater than 0.0001 wt. %.

In one embodiment, the ethyl acetate concentration in liquid stream 113 may affect first column 107 reboiler duty and size. Decreasing ethyl acetate concentrations may allow for reduced reboiler duty and size. In one embodiment, to reduce the ethyl acetate concentration (a) the catalyst in reactor may convert ethyl acetate in addition to acetic acid; (b) the catalyst may be less selective for ethyl acetate, and/or (c) the feed to reactor, including recycles, may contain less ethyl acetate.

A shown in the figures, liquid stream 113 is introduced in the upper part of first column 107, e.g., upper half or upper third. As shown, one or more extractive agents 115, as described above, are also introduced to column 107 to aid with the separation of ethanol from water (and other components). Preferably, extractive agent 115 is recovered directly or indirectly from the first residue and recycled back to first column 107, as shown in the figures, optionally with the addition of fresh extractive agent as indicated by 125. Extractive agent 115 is preferably introduced above the feed point of liquid stream 113. Extractive agent 115 is preferably introduced near the top of column 107 and flows downward until it reaches the reboiler. In some embodiments, extractive agent 115 may be heated from ambient temperature to a temperature of up to 70° C., e.g., up to 50° C., or up to 40° C. In another embodiment, extractive agent 115 is not separately preheated, but is withdrawn from other columns as shown in the FIGS. 1-7, and cooled, if necessary, to a temperature of less than 70° C., e.g., less than 50° C., or less than 40° C., and directly fed to first column 107. As shown in FIG. 6, depending on the ethyl acetate concentration of ethyl acetate recycle stream 147, this stream may be introduced above or below the feed point of liquid stream 113. In addition, extractive agent 115 may be added above ethyl acetate recycle stream 147. Depending on the targeted ethyl acetate concentration in the distillate of first column 107, the feed point of ethyl acetate recycle stream 147 will vary.

Extractive agent 115 preferably comprises water that has been retained within the system. As described herein, extractive agent 115 may be obtained from a portion of the second residue. Extractive agent 115 may be a dilute acid stream comprising up to 20 wt. % acetic acid, e.g., up to 10 wt. % acetic acid or up to 5 wt. % acetic acid. In one embodiment, the mass flow ratio of water in extractive agent 115 to the mass flow of liquid stream 113 may range from 0.05:1 to 2:1, e.g., from 0.07 to 0.9:1 or from 0.1:1 to 0.7:1. It is preferred that the mass flow of extractive agent 115 is less than the mass flow of liquid stream 113.

In one embodiment, first column 107 is a tray column having from 5 to 90 theoretical trays, e.g. from 10 to 60 theoretical trays or from 15 to 50 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 107 is operated under 50 kPa, the temperature of the residue exiting in line 116 preferably is from 20° C. to 100° C., e.g., from 30° C. to 90° C. or from 40° C. to 80° C. The base of column 107 may be maintained at a relatively low temperature by withdrawing a residue stream comprising ethanol, ethyl acetate, water, and acetic acid, thereby providing an energy efficiency advantage. The temperature of the distillate exiting in line 117 from column 107 preferably at 50 kPa is from 10° C. to 80° C., e.g., from 20° C. to 70° C. or from 30° C. to 60° C. The pressure of first column 107 may range from 0.1 kPa to 510 kPa, e.g., from 1 kPa to 475 kPa or from 1 kPa to 375 kPa. In some embodiments, first column 107 may operate at a pressure of less than 70 kPa, e.g., less than 50 kPa, or less than 20 kPa. Operating under a vacuum may decrease the reboiler duty and reflux ratio of first column 107. However, a decrease in operating pressure for first column 107 does not substantially affect column diameter.

The amount of extractive agent fed to extractive column 107 may vary widely. For example, when extractive agent 115 comprises water of diluted acid, the mass flow ratio of water to crude ethanol product may range from 0.05:1 to 2:1, e.g., from 0.07 to 0.9:1 or from 0.1:1 to 0.7:1.

The crude ethanol product in liquid stream 113 comprises ethyl acetate, ethanol and water. These compounds may form various binary and tertiary azeotropes. For example, a tertiary azeotrope may have a boiling point lower than its constituents, while other tertiary azeotropes may have a boiling point in between the pure constituents. In the embodiments of the present invention, without the use of an extractive agent, a larger portion of the ethanol would carry over into the first distillate in line 117. By using an extractive agent in column 107, the separation of ethanol into the first residue in line 116 is facilitated thus increasing the yield of the overall ethanol product in the first residue in line 116.

In this manner, ethanol, water, unreacted acetic acid, and other heavy components, if present, are removed from liquid stream 113 and are withdrawn, preferably continuously, as first residue in line 116.

First column 107 also forms a first distillate, which is withdrawn in line 117, and which may be condensed and refluxed, for example, at a ratio of from 30:1 to 1:30, e.g., from 10:1 to 1:10 or from 5:1 to 1:5. Higher mass flow ratios of water to organic feed may allow first column 107 to operate with a reduced reflux ratio.

First distillate in line 117 preferably comprises a weight majority of the acetaldehyde and ethyl acetate from liquid stream 113. In one embodiment, the first distillate in line 117 comprises a concentration of ethyl acetate that is less than the ethyl acetate concentration for the azeotrope of ethyl acetate and water, and more preferably less than 75 wt. %.

In some embodiments, first distillate in line 117 also comprises ethanol. Returning the ethanol to reactor 103 may require an increase in reactor capacity to maintain the same level of ethanol efficiency. To recover ethanol, optionally, first distillate in line 117 may be fed to an extractor and the raffinate may have a reduced ethanol concentration that can be recycled to reactor 103.

Exemplary compositions of the first distillate and the first residue for first column 107 are provided in Table 3 below. It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

EXTRACTIVE COLUMN 107

|  | Conc. (wt. %) | Conc. (wt. %) | Conc. (wt. %) |
|---|---|---|---|
| First Distillate | | | |
| Ethanol | <25 | 0.001 to 20 | 0.01 to 15 |
| Water | 0.1 to 20 | 1 to 15 | 2 to 10 |
| Acetic Acid | <2 | <0.1 | <0.05 |
| Ethyl Acetate | 10 to 85 | 15 to 80 | 20 to 75 |
| Acetaldehyde | 0.1 to 70 | 0.2 to 65 | 0.5 to 65 |
| Acetal | <3 | 0.01 to 2 | 0.05 to 1.5 |
| First Residue | | | |
| Acetic Acid | 0.1 to 50 | 0.5 to 40 | 1 to 30 |
| Water | 20 to 85 | 25 to 80 | 30 to 75 |
| Ethanol | 10 to 75 | 15 to 70 | 20 to 65 |
| Ethyl Acetate | 0.005 to 30 | 0.03 to 25 | 0.08 to 1 |

In one embodiment of the present invention, first column 107 may be operated at a temperature where most of the water, ethanol, and acetic acid are removed into the residue stream and only a small amount of ethanol and water is collected in the distillate stream due to the formation of binary and tertiary azeotropes. The weight ratio of water in the residue in line 118 to water in the distillate in line 119 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The first distillate in line 117 preferably is substantially free of acetic acid, e.g., comprising less than 1000 wppm, less than 500 wppm or less than 100 wppm acetic acid. The distillate may be purged from the system or recycled in whole or part to reactor 103. In some embodiments, when the distillate comprises ethyl acetate and acetaldehyde, the distillate may be further separated, e.g., in a distillation column (not shown), into an acetaldehyde stream and an ethyl acetate stream. The ethyl acetate stream may also be hydrolyzed or reduced with hydrogen, via hydrogenolysis, to produce ethanol. Either of these streams may be returned to reactor 103 or separated from system 100 as additional products.

Some species, such as acetals, may decompose in first column 107 so that very low amounts, or even no detectable amounts, of acetals remain in the distillate or residue. In addition, an equilibrium reaction between acetic acid/ethanol and ethyl acetate may occur in the crude ethanol product after exiting reactor 103. Depending on the concentration of acetic acid in the crude ethanol product, this equilibrium may be driven toward formation of ethyl acetate. This equilibrium may be regulated using the residence time and/or temperature of crude ethanol product.

In one embodiment, due to the composition of first residue in line 117 the equilibrium may favor esterification to produce ethyl acetate. While the esterification, either in the liquid or vapor phase, may consume ethanol, the esterification may also reduce the amount of acetic acid that needs to be removed from the process. Ethyl acetate may be removed from first column 107 or formed in situ ethyl acetate via esterification between first column 107 and second column 108. The esterification may be further promoted by passing a portion of the first residue in line 118 through an esterification reactor (not shown). The esterification reactor may be either a liquid or vapor phase reactor and may comprise an acidic catalyst. A vapor phase reactor is preferred to convert some of the first residue into an intermediate vapor feed to be introduced into second column 108.

As shown in FIG. 1, to recover ethanol, first residue in line 116 may be further separated depending on the concentration of acetic acid and/or ethyl acetate. In most embodiments, of the present invention, residue stream in line 116 is introduced to second column 108, also referred to as an "acid column," because acid, if any, from the first residue in line 116 is removed in second column 108. An acid separation column may be used when the acetic acid concentration in the first residue is greater than 1 wt. %, e.g., greater than 5 wt. %. In some embodiments, when the acetic acid concentration is low, e.g., less than 10 wt. %, the water separation column in FIG. 3 may be used.

In FIG. 1, the first residue in line 116 is introduced to second column 108, preferably in the middle part of column 108, e.g., middle half or middle third. Second column 108 yields a second residue in line 118 comprising acetic acid and water, and a second distillate in line 119 comprising ethanol. In one embodiment, a weight majority of the water and/or acetic acid fed to second column 108 is removed in the second residue in line 118, e.g., at least 60% of the water and/or acetic acid is removed in the second residue in line 118 or more preferably at least 80% of the water and/or acetic acid. An acid column may be desirable, for example, when the acetic acid concentration in the first residue is greater 50 wppm, e.g., greater than 0.1 wt. %, greater than 1 wt. %, e.g., greater than 5 wt. %.

In one embodiment first residue in line 116 may be preheated prior to being introduced into second column 108. The first residue in line 116 may be heat integrated with either the residue of second column 108 or vapor overhead of second column 108. In some embodiments, if ethyl acetate is present, esterification may be carried out in the vapor phase (not shown) that results in preheating a portion of first residue in line 116 to form an intermediate vapor feed. For purposes of the present invention, when preheating it is preferred than less than 30 mol. % of first residue in line 116 is in the vapor phase, e.g., less than 25 mol. % or less than 20 mol. %. Greater vapor phase contents result in increased energy consumption and a significant increase in the size of second column 108.

Esterifying the acetic acid in first residue in line 116 increases the ethyl acetate concentration which leads to increases in the size of second column 108 as well increases in reboiler duty. Thus, the conversion of acetic acid may be controlled depending on the initial ethyl acetate concentration withdrawn from first column 107. To maintain an efficient separation the ethyl acetate concentration of the first residue in line 116 feed to second column 108 is preferably less than 1000 wppm, e.g., less than 800 wppm or less than 600 wppm.

Second column 108 operates in a manner to concentrate the ethanol from first residue 116 so that a majority of the ethanol is carried overhead. Thus, the residue of second column 108 may have a low ethanol concentration of less than 5 wt. %, e.g. less than 1 wt. % or less than 0.5 wt. %. Lower ethanol concentrations may be achieved without significant increases in reboiler duty or column size. Thus, in some embodiments it is efficient to reduce the ethanol concentration in the residue to less than 50 wppm, or more preferably less than 25 wppm. As described herein, the residue of second column 108 may be treated and lower concentrations of ethanol allow the residue to be treated without generating further impurities.

Although the temperature and pressure of second column 108 may vary, when at atmospheric pressure the temperature of the second residue in line 118 preferably is from 95° C. to 160° C., e.g., from 100° C. to 150° C. or from 110° C. to 145° C. In one embodiment, when first residue in line 116 is preheated to a temperature that is within 20° C. of the temperature of second residue in line 118, e.g., within 15° C. or within 10° C. The temperature of the second distillate exiting in line 119 from second column 108 preferably is from 50° C. to 120° C., e.g., from 75° C. to 118° C. or from 80° C. to 115° C. The temperature gradient may be sharper in the base of second column 108.

The pressure of second column 108 may range from 0.1 kPa to 510 kPa, e.g., from 1 kPa to 475 kPa or from 1 kPa to 375 kPa. In one embodiment, second column 108 operates above atmospheric pressure, e.g., above 170 kPa or above 375 kPa. Second column 108 may be constructed of a material such as 316L SS, Allot 2205 or Hastelloy C, depending on the operating pressure. The reboiler duty and column size for second column remain relatively constant until the ethanol concentration in the second distillate in line 119 is greater than 90 wt. %.

As described herein first column 107 is an extractive column that preferably uses water. The additional water is separated in second column 108. While using water as an extractive agent may reduce the reboiler duty of first column 107, when the mass flow ratio of water to organic feed, i.e. liquid stream 113, is larger than 0.65:1, e.g., larger than 0.6:1 or larger than 0.54:1, the additional water will cause an increase in reboiler duty of second column 108 that offsets any benefit gained by first column 107.

Second column 108 also forms an overhead, which is withdrawn in line 119, and which may be condensed and refluxed, for example, at a ratio from 12:1 to 1:12, e.g., from 10:1 to 1:10 or from 8:1 to 1:8. The overhead in line 119 preferably comprises 85 to 92 wt. % ethanol, e.g., about 87 to 90 wt. % ethanol, with the remaining balance being water and ethyl acetate.

Exemplary components for the distillate and residue compositions for second column 108 are provided in Table 4 below. It should be understood that the distillate and residue may also contain other components, not listed in Table 4.

TABLE 4

| ACID COLUMN 108 (FIG. 1) | | | |
|---|---|---|---|
| | Conc. (wt. %) | Conc. (wt. %) | Conc. (wt. %) |
| Second Distillate | | | |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |
| Second Residue | | | |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 119 to ethanol in the second residue in line 118 preferably is at least 35:1. In one embodiment, the weight ratio of water in second residue 118 to water in the second distillate in line 119 is greater than 2:1, e.g., greater than 4:1 or greater than 6:1. In addition, the weight ratio of acetic acid in second residue 118 to acetic acid in the second distillate in line 119 preferably is greater than 10:1, e.g., greater than 15:1 or greater than 20:1. Preferably, the second distillate in line 119 is substantially free of acetic acid and may only contain, if any, trace amounts of acetic acid. A reduced concentration of acetic acid in line 119 advantageously provides an ethanol product that also has no amount or a trace amount of acetic acid. Preferably, the second distillate in line 119 contains substantially no ethyl acetate. The second distillate in line 119 may be withdrawn as the ethanol product or further processed to reduce water concentration.

In FIG. 1, to recover the water as the extractive agent for use in first column 107, the second residue in line 118 is further separated into a water stream and an acetic acid stream. As shown in FIG. 1 there is provided a distillation column for separating second residue in line 118, however, other separation units as shown in FIG. 4, such as an adsorption unit, molecular sieve, or membrane, may be used to separate second residue in line 118. The second residue in line 118 is introduced to a third column 109, preferably in the top part of column 109, e.g., top half or top third. The third distillate in line 121 preferably comprises water and very low amount of acetic acid, e.g., less than 5 wt. %, less than 3 wt. %, or less than 1 wt. %. The third distillate in line 121 may be returned to first column 107 as extractive agent 115 or may be purged as necessary.

Third column 109 may be a tray column or packed column. In one embodiment, third column 109 is a tray column having from 5 to 150 trays, e.g., from 15 to 50 trays or from 20 to 45 trays. Although the temperature and pressure of third column 109 may vary, when at atmospheric pressure the temperature of the third residue exiting in line 120 preferably is from 115° C. to 140° C., e.g., from 120° C. to 135° C. or from 125° C. to 135° C. The temperature of the third distillate exiting in line 121 at atmospheric pressure preferably is from 90° C. to 110° C., e.g., from 95° C. to 110° C. or from 100° C. to 110° C. The pressure of third column 109 may range from 0.1 kPa to 510 kPa, e.g., from 1 kPa to 475 kPa or from 1 kPa to 375 kPa.

In another embodiment, the acid column may also be operated in a manner that withdraws a second residue that comprises acetic acid and a second distillate that comprises ethanol and water. The water may be recovered by separating the ethanol and water. In FIG. 2, second column 122 may be a tray column or packed column. In one embodiment, second column 122 is a tray column having from 5 to 70 trays, e.g., from 15 to 50 trays or from 20 to 45 trays. When column 122 is operated under standard atmospheric pressure, the temperature of the residue exiting in line 123 preferably is from 95° C. to 130° C., e.g., from 105° C. to 117° C. or from 110° C. to 115° C. The temperature of the distillate exiting in line 124 from column 122 preferably is from 70° C. to 110° C., e.g., from 75° C. to 95° C. or from 80° C. to 90° C. In other embodiments, the pressure of second column 122 may range from 0.1 kPa to 510 kPa, e.g., from 1 kPa to 475 kPa or from 1 kPa to 375 kPa. Exemplary components for the distillate and residue compositions for second column 122 are provided in Table 5 below.

TABLE 5

ACID COLUMN 122 (FIG. 2)

|  | Conc. (wt. %) | Conc. (wt. %) | Conc. (wt. %) |
|---|---|---|---|
| Distillate |  |  |  |
| Ethanol | 10 to 85 | 15 to 85 | 20 to 85 |
| Water | 5 to 60 | 10 to 50 | 10 to 45 |
| Acetic Acid | <2 | 0.001 to 0.5 | 0.01 to 0.2 |
| Ethyl Acetate | <0.5 | <0.01 | 0.001 to 0.01 |
| Acetaldehyde | <2 | <0.01 | 0.001 to 0.01 |
| Residue |  |  |  |
| Acetic Acid | 60 to 100 | 65 to 100 | 85 to 95 |
| Water | <30 | 0.5 to 30 | 1 to 15 |
| Ethanol | <1 | <0.9 | <0.07 |

The second residue in line 123 may be recycled to reaction zone 101. In some embodiments, the water in second residue 123, if any, may be recovered and used as an extractive agent. In another embodiments, when the third residue comprises very minor amounts of acetic acid, e.g., less than 5 wt. %, the third residue may be disposed of to a waste water treatment facility without further processing. The organic content, e.g., acetic acid content, of the second distillate beneficially may be suitable to feed microorganisms used in a waste water treatment facility.

As shown in FIG. 2, the remaining water, if any, from the second distillate in line 124 may be removed in further embodiments of the present invention. Depending on the water concentration, the ethanol product may be derived from the second distillate in line 124. Some applications, such as industrial ethanol applications, may tolerate water in the ethanol product, while other applications, such as fuel applications, may require an anhydrous ethanol. Water may be removed from the second distillate in line 124 using several different separation techniques. Particularly preferred techniques include the use of distillation column, membranes, adsorption units and combinations thereof.

In one embodiment, ethanol product may be recovered after the removal of water. As shown in FIG. 2, the second distillate in line 124 is fed to a third column 126, e.g., ethanol product column, for separating the distillate into a third distillate (ethanol distillate) in line 128 and a third residue (water residue) in line 127. The third residue in line 127 or a portion thereof may be returned to first column 107 as an extractive agent. Depending on the amount of water needed as the extractive agent a portion of third residue in line 127 may also be purged. Second distillate in line 124 may be introduced into the lower part of column 126, e.g., lower half or lower third. Third distillate in line 128 preferably is refluxed, for example, at a reflux ratio of from 1:10 to 10:1, e.g., from 1:3 to 3:1 or from 1:2 to 2:1. Third column 126 is preferably a tray column as described above and preferably operates at atmospheric pressure. The temperature of the third distillate exiting from third column 126 preferably is from 60° C. to 110° C., e.g., from 70° C. to 100° C. or from 75° C. to 95° C. The temperature of the third residue in line 127 preferably is from 70° C. to 115° C., e.g., from 80° C. to 110° C. or from 85° C. to 105° C., when the column is operated at atmospheric pressure. Exemplary components of the distillate and residue compositions for third column 126 are provided in Table 6 below. It should be understood that the distillate and residue may also contain other components, not listed, such as components in the feed.

TABLE 6

ETHANOL PRODUCT COLUMN 126

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In another embodiment, preferably when acid conversion is high in reactor 103, one column may be used to recover the ethanol product and water as the extractive agent. In FIG. 3, the first residue in line 116 is fed to a second column 129, referred to as the "diluted acid recovery column." Second column 129 of FIG. 3 may operate in a similar manner as the second column of FIG. 1, to remove a substantial portion of the water in the residue. The water from first residue in line 116 may be separated into the second residue in line 132 and returned to first column 107. There may be some acetic acid in second residue in line 132 (also referred to as dilute acid stream) and a purge 133 may be taken as necessary. In some embodiments, dilute acid stream 132 may comprise at least 85% of the acetic acid from the crude ethanol product 113, e.g., at least 90% and more preferably at least 99%. In terms of ranges, dilute acid stream 132 optionally comprises from 85% to 99.5% or from 90% to 99.99% of the unreacted acetic acid from the crude ethanol product. In some embodiments, dilute acid stream 132 comprises from 2 to 60 wt. % acetic acid and from 40 to 98 wt. % water. In an embodiment, the second residue in line 132 may be return to first column 107 even if it contains acetic acid. For example, dilute acid stream 132 may contain acetic acid in an amount less than 30 wt. %, e.g., less than 15 wt. %, less than 10 wt. %, or less than 5 wt. %.

In the case where higher concentrations of acetic acid are present in—second residue 132, a water separator 138 may be used to separate water from acetic acid. For example, an adsorption unit, a membrane, a distillation column, other suitable water/acid separator, or a combinations thereof. A pressure swing adsorption unit may be used to remove water from acetic acid. Water permeable membranes that are acid resistant may also be used. In FIG. 4, the first residue in line 116 is fed to a second column 134 that operate similar to the second column of FIG. 1. The water and acid from first residue in line 116 may be separated into the second residue in line 136 and feed to a water separator 138. Water separator 138 separates second residue in line 136 into a water stream in line 139 and an acetic acid stream in line 140. In some embodiment, the water stream may comprise a small amount of acetic acid and can be referred to as a dilute acid stream. The water stream may contain acetic acid in an amount less than 20 wt. %, e.g., less than 15 wt. %, less than 10 wt. %, or less than 5 wt. %. Depending on the amount of acid in second residue 136, in some embodiments, the second residue may be purged in line 137, recycled to reaction zone 101 or treated as discussed above. As shown in FIG. 4, water stream 139 may be returned to first column 107 as an extractive agent. There may be some acetic acid in water stream 139. In an embodiment, water stream 139 may combine with fresh water 125 prior to returning to first column 107. Acetic acid stream 140 from water separator 138 preferably contains a high concentration of acetic acid. Acetic acid stream 140 may be returned to reaction zone 101.

In an embodiment, acetic acid in the second residue stream from the acetic acid column may be reacted out thereby leaving a purified water stream. In FIG. 5, second residue 132 is directed to third column 141 for esterification. In one embodiment, substantially all of the unreacted acetic acid is reacted out of second residue 132. According to embodiments of the present invention, the acetic acid present in second residue 132 is reacted with methanol stream in line 142 in esterification unit 141 to produce methyl acetate in line 143. Although methanol is shown it should be understood that other alcohols, including ethanol or mixtures of alcohols, may also be used. For example, if ethanol is used in place of methanol, ethyl acetate would be produced in line 143. As shown in FIG. 5, the esterification unit is shown as a reactive distillation column (third column) 141. Second residue 132 is co-fed to third column 141 with methanol stream 142, to produce third distillate stream 143 comprising methyl acetate and a third residue stream 144 comprising water. At least a portion of third residue stream may be purged from the system, via line 145. FIG. 5 shows methanol feed stream 142 being fed to third column 141 at a point below where second residue 132 is fed to the column. In other embodiments, methanol feed stream may be fed to third column 141 at the same level, or at a point below where second residue 132 is fed to the column.

When third column 141 is a reactive distillation column, as shown in FIG. 5, third column 141 comprises an ion exchange resin bed, an acidic catalyst, or combinations thereof. Non-limiting examples of ion exchange resins suitable for use in the present invention include macroporous strong-acid cation exchange resins such as those from the Amberlyst® series distributed by the Dow Chemical Company (e.g., Amberlyst 15®, Amberlyst 35®, and Amberlyst 36®). Additional ion exchange resins suitable for use in the present invention are disclosed in U.S. Pat. Nos. 4,615,806, 5,139,981, and 7,588,690, the entireties of which are incorporated herein by reference. In another embodiment, an acid is added to third column 141 to catalyze the esterification reaction. In this aspect, the acid may be selected from the group consisting of sulfuric acid, phosphoric acid, sulfonic acids, heteropolyacids, other mineral acids and a combination thereof. In other embodiments, acid catalysts include zeolites and supports treated with mineral acids and heteropolyacids.

In some embodiments, when an ion exchange resin is present in third column 141, second residue 132 may be fed to a guard bed (not shown) prior to being fed to third column 141. In one embodiment, the guard bed comprises an ion exchange resin, such as those disclosed above. While not being bound to any particular theory, the guard bed removes one or more corrosive metals present in second residue 132, thereby minimizing the deactivation of any ion exchange resin catalytic sites in the ion exchange resin present in third column 141.

The operating parameters of third column 141 may be varied to achieve a desired composition in third distillate 143 and/or residue stream 144. For example, in some embodiments, temperature, pressure, feed rates, and residence times can be varied to increase conversion of acetic acid to an ester, decrease the formation of impurities, achieve more efficient separation, reduce energy consumption, or combinations thereof.

In one embodiment, third column 141 operates at a base temperature of from 100° C. to 150° C., e.g., from 100° C. to 130° C., or from 100° C. to 120° C. In terms of pressure, the reactive distillation column may be operated at atmospheric pressure, subatmospheric pressure, or superatmospheric pressure. For example, in some embodiments, the reactive distillation column operates at a pressure of from 50 kPa to 500 kPa, e.g., from 50 kPa to 400 kPa, or from 50 kPa to 200 kPa.

In some embodiments, the feed rates of acetic acid and alcohol to third column 141 may be adjusted to control the mole ratio of acetic acid to alcohol being fed to third column 141. For example, in some embodiments, the mole ratio of acetic acid to methanol fed to the reactive distillation column is from 1:1 to 1:15, e.g., from 1:1 to 1:5, or from 1:1 to 1:2.

The residence time of third column 141 may impact acetic acid conversion. In some embodiments, for example, the residence time in the second column is from 1 to 5 hours, e.g., from 1 to 3 hours, or less than 1 hour.

The third distillate in line 143 exiting third column 141 preferably comprises at least 15 wt. % methyl acetate, preferably at least 35 wt. % methyl acetate, or more preferably at least 65 wt. % methyl acetate. In terms of ranges, third distillate 143 from third column 141 may comprise methyl acetate in an amount from 15 to 99 wt. %, e.g., from 35 to 90 wt. % or from 50 to 90 wt. %.

When excess methanol is reacted with the acetic acid from the dilute acid stream, some methanol also may be present in third distillate 143. Thus, third distillate 143 may comprise methanol in an amount from 0.1 to 80 wt. %, e.g., from 10 to 60 wt. %, or from 1 to 30 wt. %.

Some impurities, such as dimethyl ether may form over the course of the reaction in second column 129. These impurities may be present in very low amounts, or even no detectable amounts, in third distillate stream 143. In some embodiments, third distillate 143 comprises less than 1000 wppm dimethyl ether, e.g., less than 750 wppm, or less than 500 wppm.

Third distillate stream 143 may be fed to a carbonylation reactor for producing acetic acid, which may in turn, be used as a feedstock for the ethanol synthesis reaction. In some embodiments, third distillate stream 143 may optionally be condensed, processed, or refined, prior to being fed to the carbonylation reactor.

In one embodiment, due to the presence of ethyl acetate in second distillate 131, an additional third column 146 may be used. Third column 146, referred to as a "light ends" column, is used for removing ethyl acetate from second distillate 131 and producing an ethanol product in the third residue in line 148. Light ends column 146 may be a tray column or packed column. In FIG. 6, third column 146 may be a tray column having from 5 to 90 theoretical trays, e.g. from 10 to 60 theoretical trays or from 15 to 50 theoretical trays.

The feed location of second distillate 131 may vary depending on ethyl acetate concentration and it is preferred to feed second distillate 131 to the upper portion of third column 146. Higher concentrations of ethyl acetate may be fed at a higher location in third column 146. The feed location should avoid the very top trays, near the reflux, to avoid excess reboiler duty requirements for the column and an increase in column size. For example, in a column having 45 actual trays, the feed location should be between 10 to 15 trays from the top. Feeding at a point above this may increase the reboiler duty and size of light ends column 146.

Second distillate 131 may be fed to third column 146 at a temperature of up to 70° C., e.g., up to 50° C., or up to 40° C. In some embodiments it is not necessary to further preheat second distillate 131.

Ethyl acetate may be concentrated in the third distillate in line 147. Due to the relatively lower amounts of ethyl acetate fed to third column 146, third distillate in line 147 also comprises substantial amounts of ethanol. To recover the ethanol, third distillate in line 147 may be fed to first column 107 as an ethyl acetate recycle stream. Because this increases the demands on first column 107 and second column 129, it is preferred that the concentration of ethanol in third distillate in line 147 be from 70 to 90 wt. %, e.g., from 72 to 88 wt. %, or from 75 to 85 wt. %.

In other embodiments, a portion of third distillate in line 147 may be purged from the system as a separate product, such as an ethyl acetate solvent.

In an optional embodiment, third residue 148 may be further processed to recover ethanol with a desired amount of water, for example, using a further distillation column, adsorption unit, membrane or combination thereof, may be used to further remove water from third residue in line 148 as necessary. In most embodiments, the water is removed prior to third column 146 using water separator and thus further drying of the ethanol is not required.

Third column 146 is preferably a tray column as described above and preferably operates at atmospheric pressure. The temperature of the third residue in line 148 exiting from third column 146 preferably is from 65° C. to 110° C., e.g., from 70° C. to 100° C. or from 75° C. to 80° C. The temperature of the third distillate in line 147 exiting from third column 146 preferably is from 30° C. to 70° C., e.g., from 40° C. to 65° C. or from 50° C. to 65° C.

The pressure of third column 146 may range from 0.1 kPa to 510 kPa, e.g., from 1 kPa to 475 kPa or from 1 kPa to 375 kPa. In some embodiments, third column 146 may operate at a pressure of less than 70 kPa, e.g., less than 50 kPa, or less than 20 kPa. Decreasing in operating pressure substantially decreases column diameter and reboiler duty for third column 146.

Exemplary components for ethanol mixture stream and residue compositions for third column 146 are provided in Table 7 below. It should be understood that the distillate and residue may also contain other components, not listed in Table 7.

TABLE 7

LIGHT ENDS COLUMN (146 FIG. 6)

| | Conc. (wt. %) | Conc. (wt. %) | Conc. (wt. %) |
|---|---|---|---|
| Third Distillate | | | |
| Ethanol | 70 to 99 | 72 to 90 | 75 to 85 |
| Ethyl Acetate | 0.5 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue | | | |
| Ethanol | 80 to 99.5 | 85 to 97 | 90 to 95 |
| Water | <8 | 0.001 to 3 | 0.01 to 1 |
| Ethyl Acetate | <1.5 | 0.0001 to 1 | 0.001 to 0.5 |
| Acetic Acid | <0.5 | <0.01 | 0.0001 to 0.01 |

In some embodiments, water may be present in distillate 131, which may be carried over to the ethanol product stream 148. In one embodiment, water may be removed prior to recovering the ethanol product. In one embodiment, the distillate in line 131 may comprise less than 15 wt. % water, e.g., less than 10 wt. % water or less than 8 wt. % water. The distillate in line 131 may be fed to a water separator, which may be an adsorption unit, membrane, molecular sieves, extractive distillation column, or a combination thereof. In one embodiment, at least 50% of the second distillate in line 131 is condensed and may be fed directly to third column 146.

Figure 7:
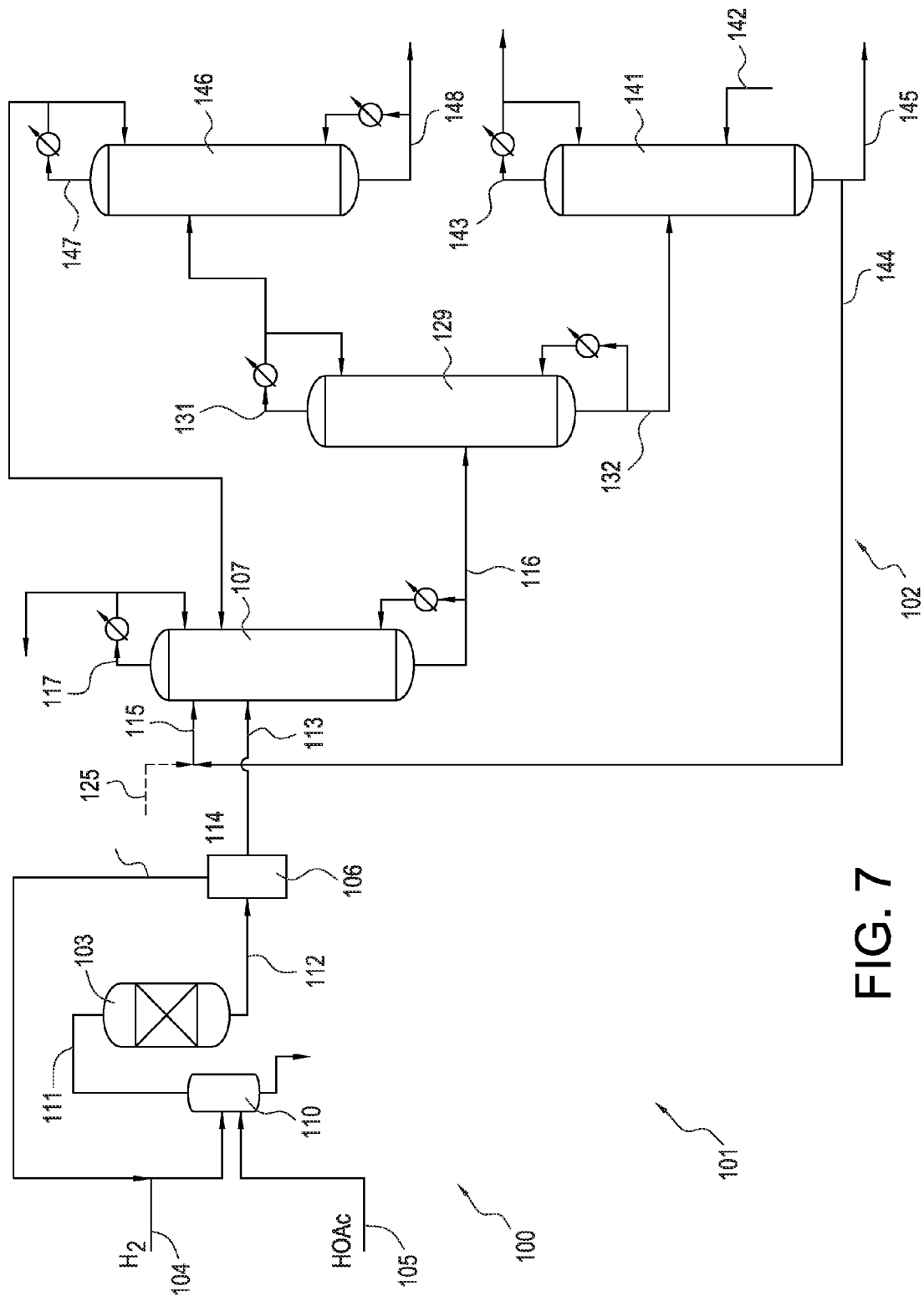
FIG. 7 is a schematic diagram of an ethanol production system similar to FIG. 6, having an esterification unit in a reactive distillation column, in accordance with one embodiment of the present invention.

FIG. 7 is a scheme showing the combination of using a reactive distillation column 141 and ethanol product column 146. In this scheme, second distillate 131 is fed to ethanol product column 146 and second residue 132 is fed to reactive distillation column 141, respectively. As a result, purified ethanol is recovered as a third residue in line 148 and ethyl acetate is recovered as a third distillate 147 and recycled to first column 107. Second residue 132 is fed to reactive distillation column 141 to react the acetic acid in the second residue with methanol to produce methyl acetate, which is recovered in line 143. Water stream 144 is recovered as a fourth residue and is returned to first column 107 as an extractive agent. At least a portion of water stream 144 may be purged from the system in line 145.

Returning to the first distillate in line 117, which comprises ethyl acetate and/or acetaldehyde, preferably is refluxed as shown in FIG. 1, for example, at a reflux ratio of from 1:30 to 30:1, e.g., from 1:5 to 5:1 or from 1:3 to 3:1. In one aspect, not shown, the first distillate or a portion thereof may be returned to reactor 103. In some embodiments, it may be advantageous to return a portion of first distillate to reactor 103. The ethyl acetate and/or acetaldehyde from the first distillate may be further reacted in hydrogenation reactor 103 or in a secondary reactor. The outflow from the secondary reactor may be fed to reactor 103 to produce additional ethanol or to a distillation column to recover additional ethanol.

In some embodiments, the first distillate in line 117 may also comprise minor amounts of water. If all or a portion of the first distillate is returned to reactor 103, it may be necessary to remove water from line 117. The water from the first distillate in line 117 may be removed, for example, by an adsorption unit, one or more membranes, molecular sieves, extractive distillation, or a combination thereof. For example, an adsorption unit (not shown) may be used to remove a water stream from first distillate in line 117 thus producing a refined light stream preferably comprising less than 1 wt. % water and more preferably less than 0.5 wt. % water. Adsorption unit may remove up to 99.99% of the water from the first distillate in line 117, and more preferably from 95% to 99.99% of the water from the first distillate. Refined light stream, or a portion thereof, may be returned to reactor 103.

In one embodiment, the first distillate in line 117, or a portion of either or both streams, may be further separated to produce an acetaldehyde-containing stream and an ethyl acetate-containing stream. This may allow a portion of either the acetaldehyde-containing stream or ethyl acetate-containing stream to be recycled to reactor 103, while purging the other stream. The purge stream may be valuable as a source of either ethyl acetate and/or acetaldehyde.

The columns used in the present invention may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns so that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Distillate in lines 119, 128, and 131 comprise ethanol, as discussed above, and may be further purified to form an anhydrous ethanol product stream, i.e., "finished anhydrous ethanol," using one ore more additional separation systems, such as, for example, distillations (e.g., a finishing column), pressure swing absorption system, membrane, molecular sieves, extractive distillation, or a combination thereof.

Any of the compounds that are carried through the distillation process from the feed or crude reaction product generally remain in the ethanol distillate in amounts of less 0.1 wt. %, based on the total weight of the ethanol distillate composition, e.g., less than 0.05 wt. % or less than 0.02 wt. %. In one embodiment, one or more side streams may remove impurities from any of the columns in system 100. Preferably at least one side stream is used to remove impurities from the third column. The impurities may be purged and/or retained within system 100.

The final ethanol composition obtained by the process of the present invention may be taken from the second distillate in lines 119, 131 or 135, third distillate in line 128, or optionally from the third residue in line 148. The ethanol product may be an industrial grade or fuel grade ethanol. Exemplary finished ethanol compositional ranges are provided below in Table 8.

TABLE 8

FINISHED ETHANOL COMPOSITIONS

| Component | Conc. (wt. %) | Conc. (wt. %) | Conc. (wt. %) |
|---|---|---|---|
| Ethanol | 85 to 99.9 | 90 to 99.5 | 92 to 99.5 |
| Water | <8 | 0.1 to 3 | 0.1 to 1 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may esterified with acetic acid. In another application, the finished ethanol composition may be dehydrated to produce ethylene.

In order that the invention disclosed herein may be more efficiently understood, an examples is provided below. It should be understood that this example is for illustrative purposes only and is not to be construed as limiting the invention in any manner.

EXAMPLES

A separation process according to this invention was used. A crude ethanol product was fed to a separation system comprising three columns. The first column was operated using water as an extractive agent and compared against a first column that did not use an extractive agent. The pressure of the first column was also tested at atmospheric pressure and vacuum at approximately 33 kPa.

The energy requirements and ethanol yield are disclosed in Table 9.

TABLE 9

|  | No Water Atmospheric | No Water Vacuum | Water Atmospheric | Water Extractive Vacuum |
|---|---|---|---|---|
| Energy Requirements [MMBtu/ton Ethanol] | 1.66 | 0.68 | 0.75 | 0.53 |
| Ethanol Recovered in Residue | 87.1% | 90.1% | 98.3% | 99.3% |

As shown in Table 9, when water was used as an extractive agent in the first column, the energy requirements for the column reduced from 1.66 to 0.75. At the same time, the amount of ethanol recovered increased from 87.1% to 98.3%. Furthermore, the cost to operate the column under reduced pressure reduced the operation cost by 36%.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising:
    hydrogenating acetic acid from an acetic acid feed stream in a reactor to form a crude ethanol product;
    separating at least a portion of the crude ethanol product in a first column in the presence of one or more extractive agents into a first distillate comprising acetaldehyde and ethyl acetate and a first residue comprising ethanol, ethyl acetate, and the one or more extractive agents;
    separating at least a portion of the first residue in a second column to yield a second distillate comprising ethanol and ethyl acetate and a second residue comprising the one or more extractive agents; and
    separating at least a portion of the second distillate to yield a third distillate comprising ethyl acetate and a third residue comprising ethanol.

2. The process of claim 1, wherein the one or more extractive agents are selected from a group consisting of water, dimethylsulfoxide, glycerine, diethylene glycol, 1-naphthol, hydroquinone, N,N'-dimethylformamide, 1,4-butanediol, ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'dimethyl-1,3-propanediamine, N,N'-dimethylethylenediamine, diethylene triamine, hexamethylene diamine, 1,3-diaminopentane, and alkylated thiopene, dodecane, tridecane, tetradecane, chlorinated paraffins, and mixtures thereof.

3. The process of claim 1, wherein the one or more extractive agents are recovered in the second residue and returned to the first column.

4. The process of claim 1, wherein at least a portion of the second residue is returned to the first column as the one or more extractive agents.

5. The process of claim 4, wherein the returned portion of the second residue comprises less than 30 wt. % acetic acid.

6. The process of claim 1, wherein the first residue comprises less than 5 wt. % ethyl acetate.

7. The process of claim 1, wherein at least one of the one or more extractive agents are co-produced in the reactor.

8. The process of claim 1, wherein at least 50% of the ethanol in the crude ethanol product is withdrawn into the first residue stream.

9. The process of claim 1, wherein the first distillate comprises from 0.001 to 20 wt. % ethanol and from 1 to 15 wt. % water.

10. The process of claim 1, further comprising separating at least a portion of the second residue to form a water stream and an acetic acid stream.

11. The process of claim 10, further comprising returning at least a portion of the acetic acid stream to the reactor.

12. The process of claim 10, further comprising returning at least a portion of the water stream to the first column as the one or more extractive agents.

13. The process of claim 1, further comprising:
    reacting the acetic acid from the second residue with at least one alcohol in an esterification unit to produce at least one ester and water; and
    separating the at least one ester from the water to produce an ester product stream comprising the at least one ester and an aqueous stream comprising water.

14. The process of claim 13, further comprising returning at least a portion of the aqueous stream to the first column as the one or more extractive agents.

15. The process of claim 1, wherein the first distillation column is operated under at a pressure of less than 70 kPa.

16. A process for producing ethanol, comprising the steps of:
    providing a crude ethanol product comprising ethanol, acetic acid, ethyl acetate, acetaldehyde, and water;
    separating at least a portion of the crude ethanol product in a first column in the presence of one or more extractive agents into a first distillate comprising acetaldehyde and ethyl acetate and a first residue comprising ethanol, ethyl acetate, and the one or more extractive agents;
    separating at least a portion of the first residue in a second column to yield a second distillate comprising ethanol and ethyl acetate and a second residue comprising the one or more extractive agents; and
    separating at least a portion of the second distillate to yield a third distillate comprising ethyl acetate and a third residue comprising ethanol.

17. The process of claim 16, wherein the one or more extractive agents are selected from a group consisting of water, dimethylsulfoxide, glycerine, diethylene glycol, 1-naphthol, hydroquinone, N,N'-dimethylformamide, 1,4-butanediol, ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'dimethyl-1,3-propanediamine, N,N'-dimethylethylenediamine, diethylene triamine, hexamethylene diamine, 1,3-diaminopentane, and alkylated thiopene, dodecane, tridecane, tetradecane, chlorinated paraffins, and mixtures thereof.

18. The process of claim 16, wherein the one or more extractive agents are recovered in the second residue and returned to the first column.

19. The process of claim 16, wherein the first residue comprises less than 5 wt. % ethyl acetate.

20. The process of claim 16, wherein at least a portion of the second residue is returned to the first column as the one or more extractive agents.

21. The process of claim 20, wherein the returned portion of the second residue comprises less than 5 wt. % acetic acid.

* * * * *